(12) United States Patent
Tass (10) Patent No.: US 8,543,219 B2
(45) Date of Patent: Sep. 24, 2013

(54) DEVICE FOR MODULATION OF NEURONAL ACTIVITY IN THE BRAIN BY MEANS OF SENSORY STIMULATION AND DETECTION OF BRAIN ACTIVITY

(75) Inventor: Peter Tass, Düsseldorf (DE)

(73) Assignee: Forschungszentrum Julich GmbH, Julich (DE)

( * ) Notice: Subject to any disclaimer, the term of this patent is extended or adjusted under 35 U.S.C. 154(b) by 1548 days.

(21) Appl. No.: 10/522,933

(22) PCT Filed: Jul. 5, 2003

(86) PCT No.: PCT/DE03/02250
§ 371 (c)(1),
(2), (4) Date: Jan. 24, 2005

(87) PCT Pub. No.: WO2004/016165
PCT Pub. Date: Feb. 26, 2004

(65) Prior Publication Data
US 2006/0047324 A1    Mar. 2, 2006

(30) Foreign Application Priority Data
Jul. 29, 2002 (DE) .................................. 10233960

(51) Int. Cl.
*A61N 1/36* (2006.01)
(52) U.S. Cl.
USPC .......................................................... 607/72

(58) Field of Classification Search
USPC .............. 600/27, 28, 45, 544, 554; 607/544, 607/554, 27, 28, 45
See application file for complete search history.

(56) References Cited

U.S. PATENT DOCUMENTS

| | | | |
|---|---|---|---|
| 3,780,724 A * | 12/1973 | John | 600/544 |
| 3,892,227 A | 7/1975 | Coursin et al. | |
| 4,171,696 A | 10/1979 | John | |
| 4,201,224 A | 5/1980 | John | |
| 4,417,592 A | 11/1983 | John | |
| 5,269,303 A | 12/1993 | Wernicke et al. | |
| 5,540,235 A | 7/1996 | Wilson | |
| 5,545,192 A * | 8/1996 | Czeisler et al. | 607/88 |
| 5,571,150 A * | 11/1996 | Wernicke et al. | 607/72 |
| 5,771,443 A * | 6/1998 | Nagano et al. | 455/115.4 |

FOREIGN PATENT DOCUMENTS

WO    WO-96/15716    5/1996

* cited by examiner

*Primary Examiner* — Christopher S Koharski
*Assistant Examiner* — Michael D Abreu
(74) *Attorney, Agent, or Firm* — Dickstein Shapiro LLP (57) ABSTRACT

The invention relates to a device for controlled modulation of physiological and pathological neuronal rhythmic activity in the brain by means of sensory stimulation, which is capable of diagnostically ascertaining functional disorders in the brain and of alleviating or eliminating the symptoms of a functional disruption. According to the invention, the device comprises a control unit (4), a stimulator (1) and at least one means for detecting brain activity, said means being connected to the control unit (1).

32 Claims, 6 Drawing Sheets

DEVICE FOR MODULATION OF NEURONAL ACTIVITY IN THE BRAIN BY MEANS OF SENSORY STIMULATION AND DETECTION OF BRAIN ACTIVITY

CROSS REFERENCE TO RELATED APPLICATIONS

This application is the US national phase of PCT application PCT/DE2003/002250, filed 5 Jul. 2003, published 26 Feb. 2004 as WO 2004/016165, and claiming the priority of German patent application 10233960.0 itself filed 29 Jul. 2002, whose entire disclosures are herewith incorporated by reference.

FIELD OF THE INVENTION

The invention relates to a device for the need-controlled modulation of physiological and pathological neuronal rhythmic activity in the brain by means of sensory stimulation.

BACKGROUND OF THE INVENTION

To diagnose the excitation processes of the brain, typically stimulation techniques like continuous excitation, is multiple single excitations and periodic excitations or stimulations have been used. For continuous stimulation, for example, continuous sound or visual patterns are considered. Individual excitations result for example in so-called acoustic or visually evoked potentials. As periodic excitation, a stimulation with flickering light can be used, for example, to diagnose a photosensitive epilepsy. Based for example on excitation responses of the brain or the sense organs as measured by means of electrodes and the psychophysical findings (for example the number of recognized patterns or heard sounds) conclusions can be drawn as to the functioning of the sensory system explored.

In biofeedback training, optical or acoustic feedback effects are therapeutically used to bring about in the patient a voluntary control of some action of the patient's bodily function, especially the sympathetic nervous system, in a desired manner. The feedback signals enable, therefore, a self-control and increase the influence upon the bodily function which pertains by the patient. Applications of biofeedback training for example include applications in functional heart conditions and neuromuscular stress states. With previous diagnostic methods, the dependency between excitation responses and the particular activity were not explored in detail. Only a relatively few parameters of cerebral activity were investigated. With the standard process it is not possible to match the stimulation to the specific rhythmic brain activity of individual patients so as to be able to detect significantly more functional and response ranges. It is especially not possible to investigate the effect of targeted manipulations in rhythmic cerebral brain activity in different frequency regions (for example their amplitude damping) and different brain areas on information processing.

It is a prerequisite of biofeedback training that the patient voluntarily and willingly desires the improved bodily function and participates therein. With most of the organ systems of the body and for many brain functions this is not the case however or is not the case to a sufficient degree. Difficulties are encountered when the patient has a cerebral disorder, for example, is a neglected patient following a brain infarct or has some other illness or medical condition following an illness which interferes with understanding or recognition and which disables a voluntary effect even on simple bodily functions, makes them more difficult or even impossible. Thus neglect patients whose body parts no longer respond can be scarcely responsive to biofeedback training at least with respect to the body parts which are nonresponsive.

Object of the Invention

It is thus an object of the invention to provide a device which enables the need-directed modulation of the physiological or pathological neuronal rhythmic activity of the brain. The device should be able to reliably and suitably diagnose functional disturbances of the brain and to ameliorate or eliminate the symptoms. In addition the device should enable brain activity, which is relevant for sensory information processes to be investigated and manipulated for diagnostic and therapeutic purposes. In addition the device should so operate that with many patients in which the illness may have resulted in at least one bodily function to be no longer capable of voluntary influence, the control of that bodily function to be improved or restored.

Object of the Invention

Starting from a device for need-controlled modulation of physiological and/or pathological neuronal rhythmic activity, these objects are attained with a control unit, a stimulator, and at least one means for detecting brain activity connected with the control unit.

With the features of the invention it is possible directly to modulate in an as-required manner the physiological or pathological neuronal rhythmic activity of the brain so that it comes close to its natural function or is identical therewith. The device is suitable for reliably diagnosing functional disturbances of the brain and symptomatically ameliorating them or eliminating them. The device enables a new diagnostic method to be carried out in which, matched to the existing or present rhythmic brain activity of a patient, a targeted manipulation of the rhythmic activity is possible in different brain regions. In this manner the neuronal information processing can be diagnostically and therapeutically explored and modulated. Furthermore, the device of the invention operates in such manner that the problem that many patients have many bodily functions which cannot be voluntarily influenced, can be overcome.

BRIEF DESCRIPTION OF THE DRAWING

The drawing shows an exemplary configuration of the device according to the invention in block diagram form for patients as well as several pulse sequences involved in the diagnosis and treatment. In the drawing:

FIG. 3 is an example of the course of the pattern over time of the sensorial excitation produced by means for generating the sensorial excitations 1.

FIG. 3 is a schematic illustration of the activity pattern of the brain region having the disorder and associated with the illustration in FIG. 3a.

FIG. 4 is a scan of the excitation frequency with which the frequency of the pulse sequence slowly varies.

FIG. 4 is a rise of the natural rhythmic activity.

FIG. is a flow diagram for the mode of operation according to the invention of the device.

SPECIFIC DESCRIPTION

Figure 1:
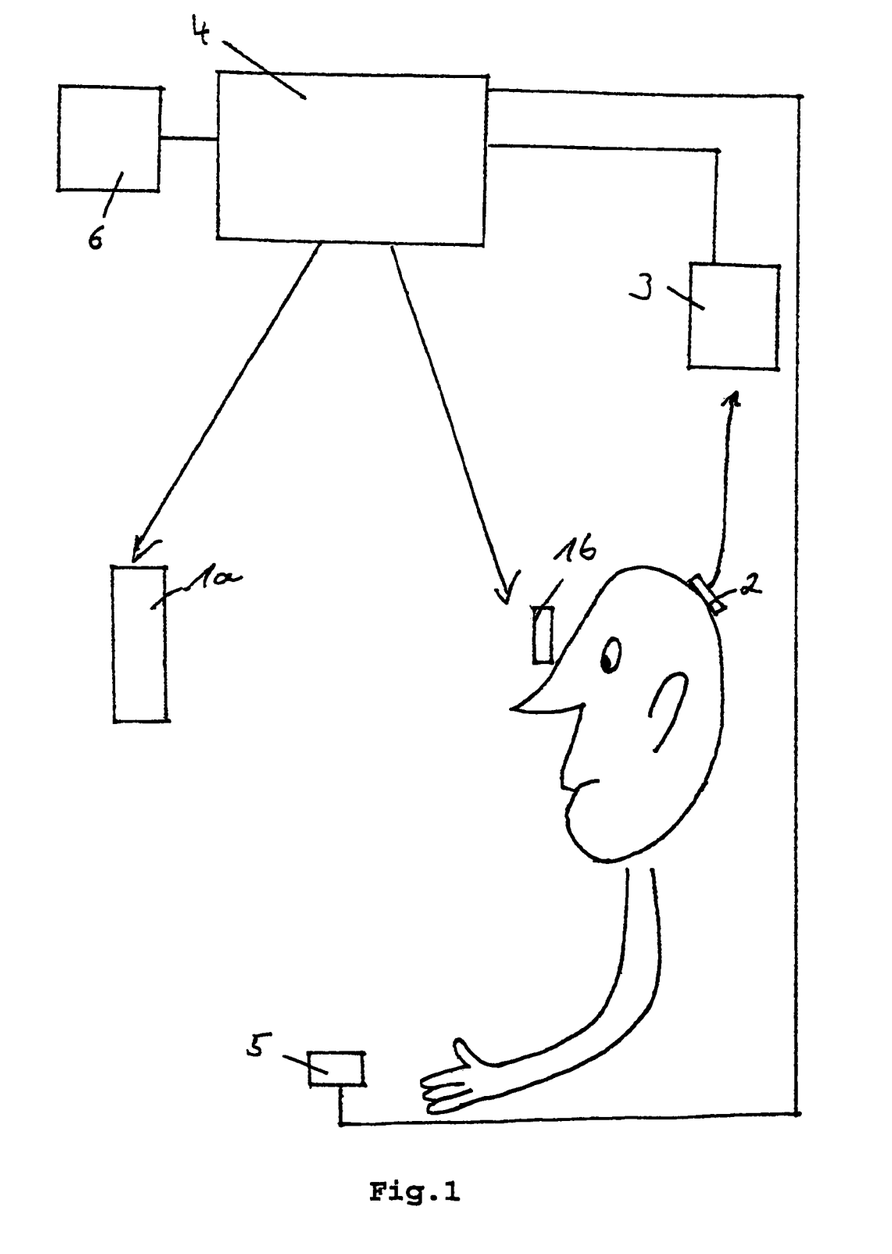
FIG. 1 is a block diagram of the device.

FIG. 1 shows a device with a stimulator 1 (1a, 1b) in front of which a patient is seated. On the head of the patient a sensor 2 is applied, the sensor 2 being connected by an isolating amplifier 3 to a control unit 4. The device comprises a receiver 5, which also is connected to the control unit 4 and which can register the reactions of the patient. In addition, the device encompasses a means for monitoring the stimulation 6 which is applied over a means for data processing and for displaying the data so that the results can be visually and/or auditorially delivered to the investigator. The control unit 4 is connected with the means 6 for monitoring the stimulation. The sensor 2, the receiver 5, the stimulator 1 and the means 6 for monitoring the stimulation can also be in a contact-free connection with the control unit 4, for example through transmitters and receivers.

Figure 2:
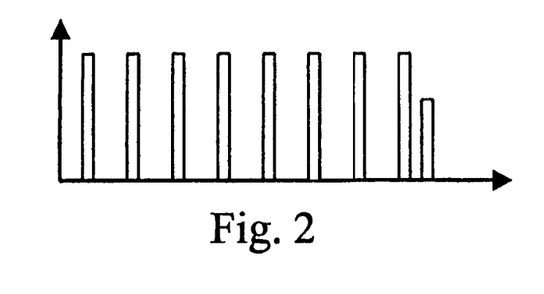
FIG. 2 is a stimulus sequence for excitation at the resonant frequency at which, for the purpose of desynchronization, a single pulse is applied in the vulnerable phase.

FIG. 2 shows a schematic pattern of a pulse sequence for a repetitive application. This pulse sequence has a periodic succession of pulses and is followed by a desynchronization pulse (last pulse). The frequency of the periodic pulse sequence is the resonance frequency of the rhythm to be desynchronized. The purpose of the pulse sequence is to effect an entrainment which controls the phase dynamic of the rhythm to be desynchronized. After a constant time interval, the desynchronization pulse is applied in the vulnerable phase of the neutral rhythm. The abscissa is a time axis in any optionally selected unit while the ordinate gives an intensity of the excitation also in any selected unit.

FIG. 3a again has an abscissa formed by a time axis in any chosen units and an ordinate which gives an intensity of the excitation also in selective units. The time segments $T_1$ and $T_2$ as well as $T_4$ and $T_5$ correspond to the configuration in FIG. 2. In the time segment $T_3$, a periodic excitation sequence is supplied whose frequency differs from the resonance frequency of the neural population to be desynchronized. In the time segments $T_1$ and $T_2$ as well as $T_4$ and $T_5$, the desynchronizing stimulation illustrated in FIG. 2 are respectively carried out.

Figure 3A:
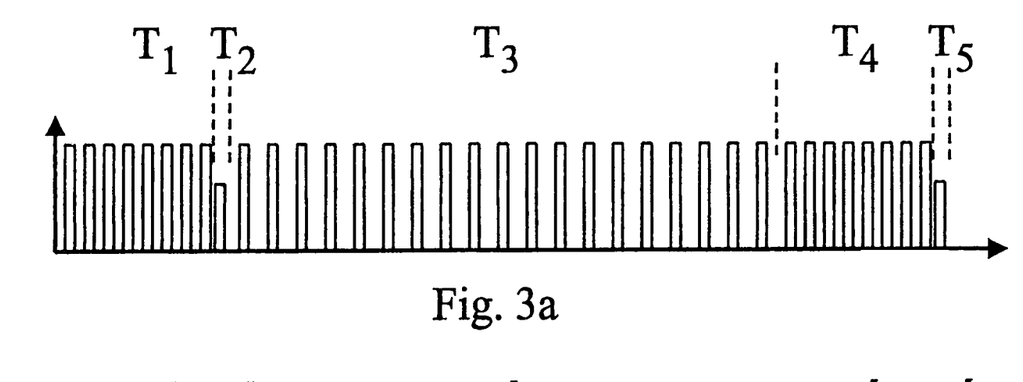
Figure 3B:
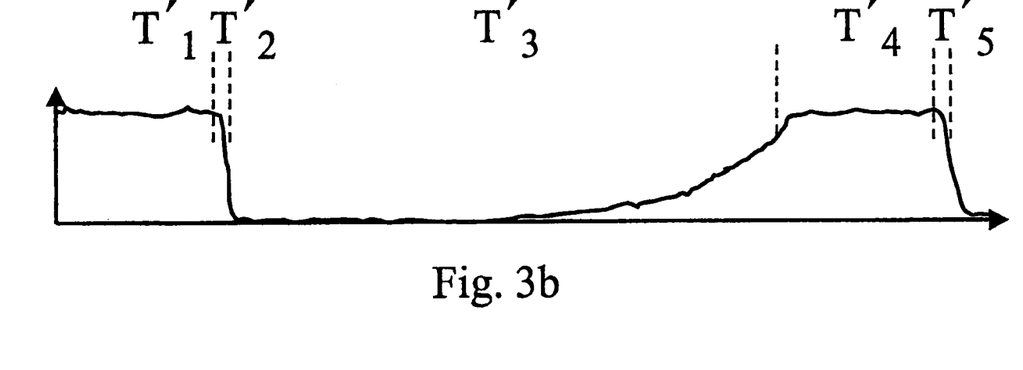

In FIG. 3b, the abscissa has a time axis which has the same time units as in FIG. 3a. The ordinate indicates schematically the amplitude as a function of time in a sliding time window of the rhythm to be desynchronized in optional units. The time segments $T'_k$ are identical with the time segments $T_k$, whereby k=1, 2, 3, 4, 5. During the entrainment in time segment $T_1$, apart from a control of the phase dynamic there is additionally a resonance-like amplification of the amplitude. The desynchronizing individual excitation in the time segment $T'_2$ encounters the neuronal rhythm in its vulnerable phase and desynchronizes it so that at the end of this stimulation the amplitude is minimal. In time segment $T_3$ there is further sensor stimulus so that the patient can accomplish his goals, for example, the detection of special patterns in an on-going manner. To maintain the suppression of the pathological rhythm as long a possible, in the time segment $T'_3$, an excitation is periodically applied at a frequency different from the resonant frequency. As soon as the amplitude of the desynchronized rhythm again exceeds a threshold value, the desynchronization step is carried out anew so that the stimulation in the time segments T' and $T'_5$ is identical with the stimulation in the time segments $T'_1$ and $T'_2$.

Figure 4A:
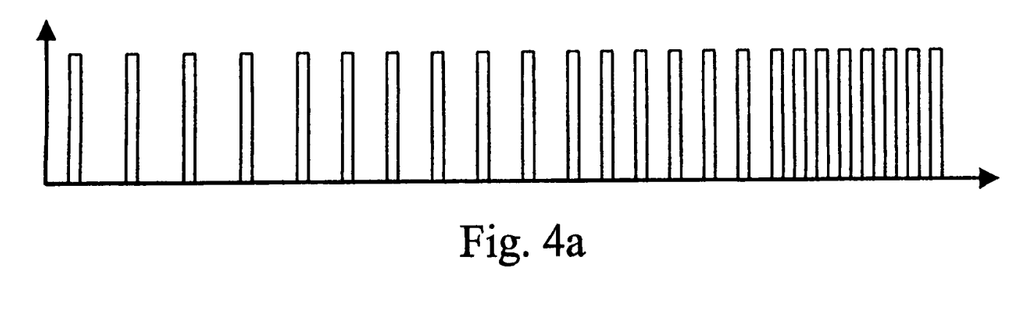

In FIG. 4a the abscissa is the time axis in arbitrary units and the ordinate gives the intensity of the stimulation also in arbitrary units. FIG. 4a shows schematically the stimulation used for the frequency scan. In this case a periodic excitation sequence is applied whose frequency varies slowly and in this example slowly increases.

Figure 4B:
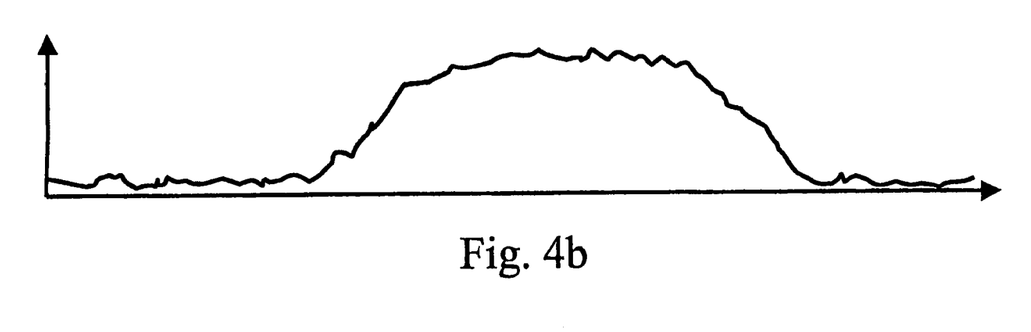
Figure 5A:
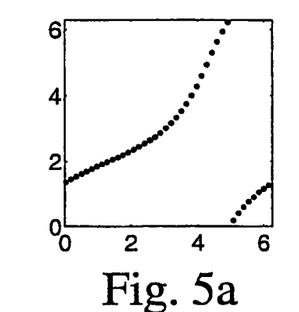
FIG. 5a—are schematic illustrations of the resetting curves of a phase associated with a standardization process.
Figure 5B:
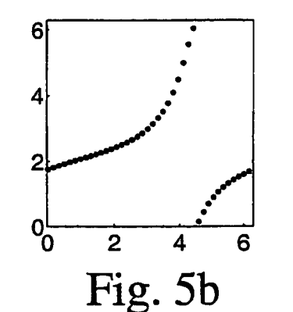
Figure 5C:
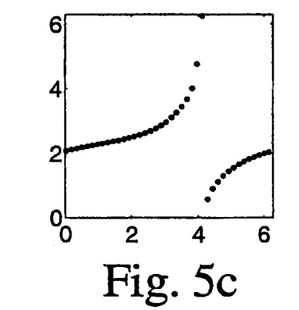
Figure 5D:
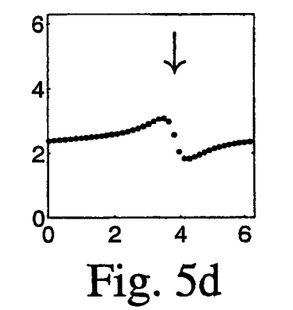
Figure 5E:
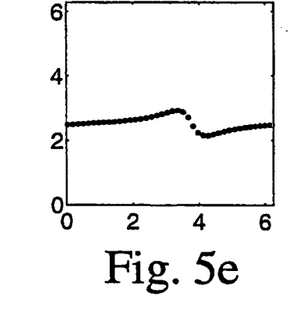
Figure 5F:
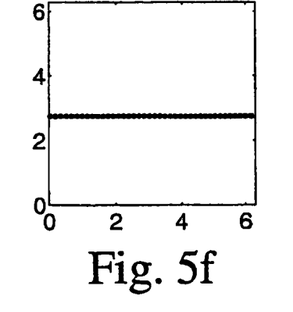

In FIG. 4b, the abscissa is the same time axis with the same units as in FIG. 4a. The ordinate indicates schematically in a sliding time window the amplitude obtained with time of the rhythm to be desynchronized, also in arbitrarily chosen units. Corresponding to the excitation frequency which is illustrated by the pulse sequence shown in FIG. 4a, a resonance frequency is produced, i.e. a resonance is generated in which the amplitude of the neuronal rhythm increases. FIG. 5 illustrates phase resetting curves in which $\phi_e$ over $\phi_b$ is illustrated. $\phi_e$ is the phase of the neuronal activity determined directly following stimulation or at a constant time delay after stimulation. $\phi_b$ is the phase of the neuronal activity determined either directly at the point in time at which the stimulation commences or at a constant time interval prior to the commencement of stimulation. The phases $\phi_e$ and $\phi_b$ are given in radians. Each partial Figure a)-f) corresponds to a series of test excitations with the same stimulus, that is an excitation with constant intensity and excitation duration, applied with different values of the starting phase $\phi_b$. The effect of the excitation on the phase dynamics for the neuronal rhythm to be desynchronized was evaluated by means of the phase resetting curves. In the partial Figures a) to c), the mean gradient of the curve was equal to 1, while in partial Figures d) to f), the mean gradient of the phase resetting curves were equal to zero. By a "mean gradient" the gradient obtained over a period of $\phi_b$ is meant. The transition between a phase resetting curve with a mean gradient 1 to a phase resetting curve with a mean gradient equal to zero is found between partial FIGS. c and d in the region of the vertical arrow with respect to the previously elevated phase $\phi_b$. This value of the phase $\phi_b$ is the vulnerable phase of the neuronal rhythm to be desynchronized. The optimum value for the intensity lies between the two intensity values of partial Figures c) and d). To obtain this value one can either select variations approximating the intensities of c) and d) or precisely generating still further phase resetting curves with intensity values between those of c) and d).

Initially there is a determination of the frequency spectrum under spontaneous conditions (1), that is without stimulation, whereby the patient is destressed and for example has his or her eyes open for 5 minutes and the eyes closed over a further period of 5 minutes. With open or closed eyes, is respective brain rhythms which are especially strong or especially weak are obtained. For example the $\alpha$ rhythm is typically more strongly expressed with closed eyes and more weakly expressed by contrast with open eyes. A strong expression of a neuronal rhythm means that this rhythm especially has a large amplitude. In this manner the point width of the expression of the physiological or pathological rhythms which arise without stimulation can be determined.

Next a frequency scan is carried out (evaluation of the strength of the resonance by means of an amplitude determination of the excited rhythm), possibly together with determination of the quality of the entrainment over determination of the strength of the phase synchronization between the excitation sequence and the excited rhythm.

Depending upon the results from (1) and (2), either of two different processes develop. In case the patient's natural and nonpathological rhythmic activity is too weakly expressed or is mainly not present, a need-controlled synchronization is carried out in steps (3-5). In case the patent has a pathological rhythmic activity, a need-controlled desynchronization is carried out in steps (6-9).

The need-controlled synchronization (3) can be carried out in turn in two ways: in the context of a simple control function, at the beginning of a sensory stimulation the excitation frequency $f_A$ and the intensity are established and maintained constant during the stimulation (4). In a preferred embodiment of the invention the stimulation is commenced by values suitable for step (2) of the excitation frequency $f_A$ and the intensity (5). The control unit 4 matches however in this mode the parameters (especially the intensity) as controlled by need.

For the need-controlled desynchronization, initially the quality of the entrainment evaluated (6) and then a determination is made of the vulnerable phase (7), which—as described below—is associated with a determination of the optimum excitation intensity or excitation duration. The need-controlled desynchronization can then be effected in two ways: either a repetitive application of the sensory stimuli (8) is carried out or a restraining application is carried out (9). During repetitive application (8), the same desynchronizing excitation sequence is repetitively supplied whereas in the pauses therebetween no excitation is effected. During the continuous application (9) by contrast, sensory stimuli are continuously applied and upon exceeding the threshold of the neuronal activity to be desynchronized, the same desynchronizing excitation sequence is always applied.

In practically all of the steps, through the means for visualization (FIGS. 1 and 6) a feedback to the investigator can and should be provided.

Below the components of the device according to the invention are described in detail and their functions explained.

The stimulator 1 is an excitation pulse generator which produces signals which can be consciously or unconsciously perceptible to the patient. Basically in this manner all signals which can be sensorially processed by patients can be generated. For example, visual excitation signals, acoustic excitation signals or signals which excite the sense of taste or, less probably, signals which evoke the pain sense can be mentioned. Visual excitations can include images or patterns. The visual excitations can be outputted, for example, through a special is display screen 1a or spectacles or glasses provided with shutters 1b. The display screen can for example be a projection screen which through a shutter diaphragm with a projector which displays a continuous image over time, provides the sensory response. The light-blocking mechanism for the shutter glasses or spectacles and the shutter for the projector screen can operate preferably either in accordance with the LCD technique or FLC (ferroelectric liquid crystal) technique. The images and patterns which are used to evoke the visual responses can be those known to the artisan. They can be, for example, Kanisza figures.

All tones or complex noises or sounds can be used as acoustic stimuli, like for example iterations of time-delayed broad band noise or sounds in the audible frequency range which can be outputted by a loudspeaker 1c or head phones 1d. An excitation stimulator which can excite the sounds of taste or pain sensitivity can for example be a somatosensoric stimulation generator 1e or a time-modulated laser 1f. An excitation generator in the sense of the invention is thus a device for producing a visual, acoustic or another sensory signal or stimulus. The stimulator 1 can output the signals described in a time-based pattern either rhythmically or arrythmically. This means that visual images or patterns can be produced in a periodic sequence in time-spaced intervals of preferably 1 to 100 Hz or 1 to 70 Hz and/or in complex nonperiodic time-based sequences although the application is not limited to these frequencies. Furthermore the intensities or amplitudes of the signals can also be varied. With visual excitations, not only can the brightness be varied but the contrast can be varied as well. Analogously tones can be applied in a periodic time-based sequence of preferably 1 to 100 Hz and/or in complex nonperiodic time-based sequences. In addition, the sound amplitude can be varied. Analogously the same applies for the means for generating the other sensory stimuli in which pressure and frequency can be varied. The complex nonperiodic time-based sequence of individual sensory excitations can, as described below, derive for example from a combination of a periodic excitation sequence with subsequent qualitatively individual excitations.

In health there is typically rhythmic activity in certain frequency bands and which arises in certain brain areas, for example one can observe so-called a rhythm (ca. 10 Hz) preferentially in the region of the visual cortex. In patients, these physiological rhythms on the one hand may be less expressed or pronounced or on the other hand may have pathological rhythms present in them and which are characterized by atypical meaning nonphysiological frequency bands. A pathological rhythm can also be characterized by a normal frequency content but nontypical anatomical localization. A pathological rhythm need not only be limited to a single brain region but can also affect other anatomically connected brain regions by feeding the pathologically rhythmic activity thereto and affecting their functions.

The frequency content of the brain activity of the patient has been characterized by the investigator, physiological rhythms which are insufficiently distinct can be excited or excessively pronounced pathological rhythms can be suppressed or weakened. If pathological rhythms are weakly expressed or pronounced, predominantly periodic stimuli, which are outputted by the stimulator 1, can excite these rhythms. In a further step, through stimuli a desynchronization of the pathological rhythmic activity can be effected. Then the signal sequences which are to effect the desynchronization can differ from those which enable the analysis or diagnosis in that these may tend to increase the pathological rhythmic activity. For desynchronization at least one desynchronizing pulse is produced.

The signals which are outputted by the stimulator 1 modulate rhythmic activity in certain brain areas in a manner which can be detected by the sensor 2. The sensor 2 is in this sense a means for detecting brain activity. As examples of them, scalp-EEG electrodes are MEG sensors, that is SQUIDS, can be mentioned. The apparatus is equipped according to the invention with at least one sensor which is connected with the control unit 4.

The control unit 4 processes the signal obtained from the sensor 2. The control unit 4 operates through means for carrying out the processed steps which have been described in the application. This means can be especially a computer or an electronic circuit together with a computer programmer a programmable processor like, for example, a FPGA (field programmable array) which is capable of carrying out the steps according to the invention of signal collection and evaluation and can control the stimulator 1 in the manner required by the invention.

It is especially advantageous to be able to practice the method with suitable processors. The term "processor" should not however be understood to be limited in any sense. It can be for example any optional unit suitable for carrying out computations. It is possible for the processor to comprise a multiplicity of individual processors which are advantageously assembled into an appropriate processor unit.

In the sense of the present invention, in addition, any circuitry suitable for computation can be used. Advantageously, the circuit can be built into a computer or incorporated in a logic component. The means of the description for carrying out the method steps of the invention are components of the control unit 4 encompassing at least one component from the group comprised of a computer, an electronic circuit, a computer program or a processor. The means for controlling the different method steps need not however be provided in a single device.

The control unit 4 determines the degree of expression or development of a pathological rhythmic activity. If the pathological activity is not present or is present only minimally, the control unit 4 provides control signals to the stimulator which can then output either no stimuli or other stimuli which differ either in frequency or amplitude or in frequency and amplitude from prior stimuli. In a diagnostic application the frequency and/or amplitude of the stimuli are varied until the pathological reaction is a maximum, that means that the rhythmic reaction of the pathological brain area is the strongest. This has the advantage that otherwise possibly imperceptible pathological rhythms can be recognized under certain conditions in case at the point in time of the diagnostic investigation they might otherwise be too weak. In this case the control unit operates through means capable of calling up a maximum physiological and/or pathological brain activity. This means operating for example through an electronic circuit, a processor or a computer and associated software, ensures that stimulation sequences are provided as described below. The pathological rhythmic activity pattern is analyzed by the control unit 4. The control unit 4 is adapted to provide another time-based pattern of the stimulus which is targeted to modulate the pathological activity and especially to suppress the pathological activity pattern or to attenuate it. Thus, opposite to the first effect, namely the promotion of the pathological activity, damping and, especially preferably, a complete suppression of the pathological brain activity is effected. The sensor 2 continues to detect the brain activity and with the control unit 4 analyzes the new state of the brain. Through a number of cycles of this type the control unit 4 is able to determine the stimuli with which the pathological conditions can be suppressed as completely as possible.

The receiver 5, which serves for patient control is connected with the control unit 4. The receiver 5, in the sense of the invention can be for example a push button or a switch or lever which is actuated by the patient. The patient is instructed to actuate the receiver 5 in response to certain signals. In this manner the ability of the patient to perceive the sensory stimuli or the treatment effect and the reaction to the procedure can be controlled. The signals from receiver 5 are computed or processed in the control unit 4 and are transmitted to the means 6 for monitoring the stimulation. Through these means 6 the investigator can determine the quality of the stimulation and the result of its application to the patient. The device according to the invention equipped with the receiver 5 and the means 6 for monitoring stimulation constitutes thus a preferred embodiment of the invention.

In the application of the apparatus, two cases A and B can be distinguished and are explained below by way of example.

A: For patients who naturally have nonpathological rhythmic activity which is expressed too weakly or primarily or is usually not present.

B: The patient presents with a pathological rhythmic activity in at least one region of the brain.

In cases A and B, the control unit 4 operates in the following manner:

Frequency Scan

The frequency scan both in case A and in case B is carried out initially. In the frequency scan, a periodic sensory stimulation with an excitation frequency $f_A$ is carried out in which $f_A$ varies slowly between preferably 1 and 100 Hz, especially preferably between 1 to 60 Hz. In FIG. 4a this has been reproduced by way of example with an increasing frequency of the applied signal sequence. Sensor 2 measures the neuronal activity and supplies it to the control unit 4 which determines in which frequency range the neuronal activity develops an excitation. This excitation can the be quantified by (i) integrating the amplitude of the power spectrum over the excited frequency range or, analogously thereto (ii) determining the instantaneous amplitude of the frequency range by means of the Hilbert transformation.

The device of the invention thus comprises means for carrying out a frequency scan as well as means for carrying out the step (i) and/or (ii).

The electronic circuitry used for example for this purpose or equivalent means in control unit 4, as well as a computer program, which for example operates in accordance with the methods (i) and (ii) can serve as the means for quantifying the neuronal activity.

This frequency scan can be carried out by the control 4 which activates the means for generating sensor stimuli 1 so that the respective frequency is reproduced in the patient in the form of a sensory stimulus. For this purpose the control unit 4 can act through means for controlling the stimulator 2, for example a TTL pulse generator. The control unit 4 recognizes the signals captured by the sensor 2 or their amplitudes in the investigative frequency range at which the excitation frequency produces a maximum excitation. The device thus comprises advantageously such means which is capable of investigating in the signals measured by the sensor 2 apart form the frequency range of the excitation frequency also other frequency ranges. This means can carry out time-dependent frequency analysis based upon Fourier transformation or wavelet analysis. For this purpose the control unit 4 comprises a means which is suitable for carrying out these steps. Such means can be as has been described above by say of example, a computer, an electronic circuit, a processor, a programmable electronic circuit (FPGA) or a computer program. The frequency of the excited activity can thus coincide with the excitation frequency or can also not coincide therewith. Surprisingly it has been found that the frequency of the periodic stimulus sequence which serves for entrainment follows the law given below:

$$f_R/f_A = n/m \qquad \text{Formula 1}$$

where $f_A$=the excitation frequency, that is the frequency of the periodic stimulus sequence serving for excitation $f_R$=the frequency of the excited neuronal activity (resonance frequency)

whereby n and m are small whole numbers, that means <10, (namely 1, 2, 3, 4, 5, 6, 7, 8, 9, 10) for example, n/m=1/1, ½, ⅔ etc.

With the aid of the frequency scan, two aspects of the is excitation properties are explored.

1. A determination is made as to whether an excitation will bring about a physiological rhythm in a frequency range expected for this rhythm. With flicker light stimulation, these frequency ranges can be for example in the region of 10 Hz, 20 Hz, 40 Hz and 80 Hz. In this case a determination is made whether a physiological rhythm, which may be of pathological origin or can develop spontaneously, that is without stimulation, is too weakly expressed, can be excited by periodic stimulation.

2. A determination is made as to whether an excitation will lead to a pathological rhythm. The latter is characterized by a physiological response that does not lie in a physiological frequency range or is in a physiological frequency range but arises at an untypical brain region. The physiological frequency ranges are the frequency ranges at which neuronal rhythms naturally occur. For example, the α rhythm in the region of about 10 Hz and rhythm in the region of about 20 Hz can be mentioned. In this manner a determination is made as to whether a pathologically generated rhythm can be produced by a periodic stimulation. Such pathological rhythm is typically, although not necessarily already present under spontaneous conditions, that is without stimulation.

After the frequency scan is carried out as described above, the application of the invention is effected in accordance with cases A and B below.

A. Need-Controlled Synchronization

The goal of the need-controlled synchronization is, with patients who have one or more too weakly expressed physiological rhythms to excite that by sensor stimuli during treatment. For this purpose the stimulus treatment which is found to be required because of the weakened physiological rhythm is improved or enabled. For this purpose the sensor 2 registers the neuronal activity of the brain area to be excited. The signals measured by the sensor 2 are advantageously supplied to the control unit 4 through an isolating amplifier 3. The control unit 4 can then control the sensor stimulation in two different ways:

1.) In the framework of a simple control function, at the beginning of the sensory stimulation the sensory stimuli or pulses are applied with an excitation frequency $f_A$ and the intensity according to the results of the frequency scan. These stimulation parameters remain constant during the sensory excitation.

2.) As under (1), the excitation is commenced with an excitation frequency $f_A$ and the intensities which are appropriate from the results of the frequency scan. The control unit 4 matches these parameters during the sensory excitation under need control. That means that the control unit 4 reacts to a decrease in the amplitude of the rhythm to be excited with an increase in the intensity of the exciting stimulus. In this case the control unit 4 acts through means for registering the change in the amplitude of the rhythm which is to be excited to change the excitation intensity. For this purpose as has been described by way of example above, a computer, an electronic circuit, a processor, a programmable electronic circuit (FPGA) or a computer program can be used. The range of intensities used in this case is limited at its upper level by safety consideration, this means an avoidance of the triggering of an epileptic response.

During the sensory stimulation described under (1) or (2), the patient is subjected to defined stimuli like, for is example Kanisza figures. The patient is previously instructed to look for special features in these stimuli. By feedback over the push button 5, the patient can control whether the recognition of the sensory stimulus to which the patient is subjected is improved or enabled by the excitation of the physiological rhythm. By at least one and preferably three hiatuses in the reaction of the patient, a suitable signal from the control unit 4 is provided to the means 6 for monitoring the stimulation and thus supplied to the investigator. This signal serves to let the investigator know when the patient is not willing or is not in a position to process the sensory stimulation in accordance with the predetermined requirements as set out above.

B. Need-Controlled Desynchronization

The goal of the need-controlled desynchronization is to damp or suppress one or more pathological rhythms which may be too strongly active or expressed during the processing of sensory stimuli. For this purpose, the stimulus processing which may be destroyed by an excessively expressed neuronal rhythm should be improved or enabled. This result is achieved with the device according to the invention and especially with the control unit 4 or the above-described means forming part thereof and functioning as described in the following.

The sensor 2 registers, for this purpose, the neuronal activity of the brain area to be damped. The signals measured by the sensor 2 are supplied to the control unit 4, preferably through the isolating amplifier. The control unit 4 operates, according to the invention, in accordance with the following principle:

A rhythmically active neuronal population can be desynchronized with a sensory stimulus when the stimulus or is excitation on the one hand has the correct intensity and duration and, on the other hand, is applied in a critical phase of the corrective oscillation of the neuronal population, the so-called vulnerable phase. Because of the unavoidable variability of the frequency of a neuronal population, it is difficult to determine precisely the vulnerable phase. The problem is solved in accordance with the invention by the use of complex stimuli. These are comprised of two qualitatively different stimuli or excitations or pulses:

The first stimulus controls the dynamics of the neuronal population such that at the end of this stimulus the dynamic state of the neuron population is known with sufficient precision. For this purpose an entrainment is carried out, that is, an entraining periodic stimulus for excitation sequence is applied in order to bring the dynamics of the neuron population into step with the stimulus sequence. To this end, the device according to the invention, through means for effecting an entrainment, that is a periodic stimulation for the purpose of controlling the rhythm, meaning the phase dynamic, can control the excitation of the neuronal activity. This can be achieved as has been indicated in greater detail by example above, with a computer, an electronic circuit, a processor, a programmable electronic circuit (FPGA) or a computer program.

The second stimulus or excitation follows the first, entraining stimulation (the stimulation sequence) with a substantially constant time lag. It encounters the pathologically synchronized, neuronal population in a vulnerable state and gives rise, in this way, to a desynchronization. The second stimulus or excitation pulse is comprised advantageously of only a single stimulus or excitation pulse, or a short periodic stimulus or pulse sequence, which can be comprised of at least two individual stimuli or pulses and advantageously not more than ten individual stimuli or excitation pulses. To this end, the device of the invention is provided with means for desynchronization. Such means, as has also been indicated by example above, can be a computer, an electronic circuit, a processor, a programmable electronic circuit (FPGA) or a computer program which is capable of carrying out the process steps described below.

The stimulation parameters required for the desynchronization are determined in accordance with the invention by the following standardization procedure.

1.) Monitoring the Quality of the Entrainment:

a stimulus for excitation pulse sequence comprised of k preferably identical stimuli or excitation pulses are applied one time, preferably ten to one hundred times. In this case, n small values are varied as above until the entrainment is good enough. The quality of the entrainment is then investigated in the following manner or quantified:

the phase and the amplitude of the neuronal rhythm to be desynchronized are determined preferably by the Hilbert transformation. An alternative method can be the matching in a sliding time window of the signal of the neuronal rhythm with a slowly varied sine function. For this purpose, the device according to the invention is provided with means for testing the quality of the entrainment. Such means can be, as has been indicated in an exemplary way above, a computer, an electronic circuit, a processor, a programmable electronic circuit (FPGA) or a computer program which carries out the described steps.

The effect of the entrainment is that after the entraining stimulation, the neuronal rhythm will always have the same amplitude and above all always the same phase, independent of the amplitude and the phase at the beginning of the stimulation. To ensure that this will be the case, the phase or preferably the phase and amplitude are evaluated by means for evaluating phase and amplitude or in a less preferred embodiment of the invention, exclusively by means for evaluating the phase of the neuronal rhythm in the following manner. For this purpose as has been described above by way of example, the described steps can be carried out by a computer, an electronic circuit, a processor, a programmable electronic circuit (FPGA) or a computer program.

For the first applied stimulus or excitation pulse sequence, which is comprised of n individual stimuli or excitation pulses, the means for carrying out a phase resetting can produce a so called phase-resetting curve. A phase resetting curve is a phase response curve in which the phase at the end of the stimulation for all m applied excitation or stimuli sequences. A perfect entrainment is obtained when a horizontal phase resetting curves, that is a phase resetting curve which is independent of the phase at the beginning of the stimulation always assumes the same value as the phase at the end of the stimulation.

The phase resetting curve can be displayed to the researcher for example by a display screen forming a means for visualization 6. On the other hand, the phase resetting curve can be used to evaluate the value of the phase at the end of the stimulation, for example by a simple mathematical operation like determination of the standard deviation of the value of the phase, or the quality of the match of a horizontal line to the phase resetting curve by means for the quantitative characterization of the phase resetting curve. Such means, as has also been indicated in an exemplary manner above, can be a computer, an electronic circuit, a processor, a programmable electronic circuit (FPGA) or a computer program which is designed to carry out the described steps.

Preferably the quality of the entrainment is determined exclusively visually by the investigator through the means for monitoring the stimulation 6. The amplitude is determined in the same way by means of amplitude resetting curves. The device of the invention can then include means for determining the amplitude and for carrying out an amplitude resetting which operates in the following manner. For this purpose the apparatus can include, as was described above in an exemplary manner, a computer, an electronic circuit, a processor, a programmable electronic circuit (FPGA) or a computer program which can carry out the above-described steps. In the amplitude-resetting curves, that is amplitude response curves, the amplitude at the end of the stimulation is plotted against the amplitude at the beginning of the stimulation for all m applied stimulation or excitation sequences. A perfect entrainment leads to a horizontal amplitude resetting curve, that means, independent from the amplitude, at the beginning of the stimulation the amplitude at the end of the stimulation will assume always the same value. The amplitude resetting curve is evaluated like the phase resetting curves quantitatively and/or and preferably only visually.

The number of stimuli or excitation pulses following one another in a pulse sequence k is increased until the entrainment is sufficiently good in terms of amplitude and phase.

In an alternative and preferred embodiment of the invention the quality of the entrainment is examined in the following manner and quantified. The goal of this alternative procedure is to monitor the quality of the entrainment not only at the end but during the application of the entire stimulus or excitation sequence. This makes the determination of the quality less dependent on fluctuation of the measured neuronal dynamic which can be affected either by the measurement process or above all by intrinsic neuronal noise. For this purpose, a stimulus sequence comprised of k preferably identical stimuli or excitation pulses is applied one time and preferably ten to one hundred times. K is then varied by small values as described above until the entrainment is good enough. The quality of the entrainment is investigated or quantified in the following manner:

The signal representing the excited neuronal activity measured by the sensor two is filtered in a band pass filter which completely contains the frequency peak $f_R$ (formula 1) of the resonance frequency but does not contain other frequency peaks, the harmonics, subharmonic or other physiological or pathological rhythms. Using the Hilbert transformation, the phase $\phi_R$, that is the phase which is determined from the band pass filtered signal in this manner. Apart from this, the phase $\phi_A$ is determined, that is the phase of the excitation stimulus sequence or excitation sequence. This can be achieved in two ways: either a sine function can be matched to the stimulus sequence such that the maximum of the signed function will coincide with the point in time at which the individual stimulus is applied. The phase $\phi_A$ is then the phase of the matched sine function. Alternatively, the signal which represents the stimulus sequence and thus the sequence of rectangular pulses which correspond to the excitation frequency $f_A$ of formula 1 and the band pass filter is selected. The phase $\phi_A$ is then the phase determined by the Hilbert transformation of the band pass filter signal of the stimulus sequence. The band pass used for this purpose must be so selected that it completely encompasses the frequency peak $f_A$ in the spectrum of the signal of the excitation sequence but contains no other frequency peak. Then the n:m phase difference $n\phi_A - m\phi_b$ between the excitation stimulus sequence and the excited neuronal activity is determined. The strength of the entrainment is then preferably determined by means of the n:m-entrainment index which is defined as follows: in the time window used for determining the quality of the entrainment, the distribution of the n:m phase difference is determined. The entropy S of this distribution is then determined according to the formula 2

$$S = -\sum_{k=1}^{N} p_k \ln p_k \qquad \text{(Formula 2)}$$

whereby, $p_k$ is the relative probability that the value of the n:m phase difference will be found in the k the case bin. The number of the bins N is typically determined in accordance with formula 3:

$$N = \exp[0.626 + 0.4 \, \text{Ln}(M-1)] \qquad \text{(Formula 3)}$$

whereby M is the number of measured values of the n:m phase difference during a stimulus sequence.

The n:m entrainment index $e_{n,m}$ is calculated in accordance with formula 4

$$e_{n,m} = \frac{S_{max} - S}{S_{max}} \qquad \text{(Formula 4)}$$

whereby $S_{max}$ is the entropy of an equilibrium, that is $S_{max} = \ln N$, whereby the optimum number for determining the distribution in terms of equidistance partial intervals or bins is given by the formula 3. Through the means of formula 4 a normalization is carried out such that $0 \leq e_{n,m} \leq 1$. $e_{n,m} = 0$ means that no entrainment is present while $e_{n,m} = 1$ corresponds to a perfect entrainment. The larger the value of $e_{n,m}$, the better is the entrainment.

Values of $e_{n,m}$ are obtained for each applied stimulus sequence. From that value the mean value $$E_{n,m} = \frac{1}{l} \sum_{j=1}^{l} e_{n,m}^{(j)} \qquad \text{(Formula 5)}$$

is calculated whereby $e_{n,m}^{(j)}$ is the j—the stimulus sequence. The relationship $0 \leq E_{n,m} \leq 1$ applies. The number of the k stimuli or excitation pulses in a stimulus sequence following one another is increased until the entrainment is sufficiently good, that is until $E_{n,m}$ sufficiently approaches one.

2.) Determining the Vulnerable Phase:

The vulnerable phase depends upon the intensity and the duration of the sensory stimulation. Advantageously the duration of the sensory stimulus is held constant in the frame work of the standardization procedure while the intensity and the vulnerable phase are so varied, as described below, that the desynchronizing effect of the stimulation is maximized.

The determination of the vulnerable phase is carried out with means for determining the vulnerable phase. Such means, as has been indicated above by way of example previously, can be a computer, an electronic circuit, a processor, a programmable electronic circuit (FPGA) or a computer program which can carry out the steps described in the following. In this case the device according to the invention can operate in two different ways:

A) the time spacing between the last stimulus or excitation pulse of the entraining stimulus or excitation pulse of sequence and the desynchronizing pulse on the one hand and the intensity of the desynchronizing stimulus are varied by means for varying the time spacing between the last stimulus of the entrainment and the desynchronizing stimulus between preferably 0 and 2 period lengths of the mean frequency of the frequency band associated with the pathological rhythm in a systematic manner, preferably in small equidistant steps. The means used for this purpose as has been described by way of example above, can be a computer, an electronic circuit, a processor, a programmable electronic circuit (FPGA) or a computer program. This variation in the time spacing is carried out systematically for different values of the intensity by means of a means for varying the intensity. Preferably the intensity is increased in small equidistant steps and for each value of the intensity, the time spacing is determined as described above between 0 and 2 period lengths. The variation of the time spacing and the intensity is carried out preferably by the control unit 4. The optimum value for the intensity of the sensory stimulus and the time spacing between the last stimulus of the entrainment and the desynchronizing stimulus is the value at which the strongest desynchronization effect arises, that is the amplitude at which the desynchronized rhythm after stimulation is the smallest. The amplitude is preferably determined by band pass filtration with subsequent Hilbert transformation.

Alternatively, the amplitude can be determined either by a matching of a slowly varying sine function to the band pass filtered signal of sensor two in a time window after stimulation or by determining the integrated amplitude over the frequency band of the power spectrum of sensor two in a time window after stimulation.

B) The time spacing is varied under A). Differing from A), the intensity is not increased in equidistant steps but is varied systematically in the following way: in this case phase resetting curves are used with which the effect of the desynchronizing stimulus on the phase dynamics of the neuronal activity to be desynchronized is investigated. The phase is advantageously determined by means of band pass filtration and a subsequent Hilbert transformation of the signals measured by the sensor two. Alternatively to the use of the Hilbert transformation, a slowly varying sine function in a sliding time window can be matched to the band pass filter signal of sensor two.

The limits of the pass band can then be the limits of the frequency band of the pathological neuronal rhythm which is determined at the outset. When reference is made to the phase resetting curves, $\phi_e$ over $\phi_b$ are obtained by a means for applying $\phi_e$, the phase of the neuronal activity after stimulation, over $\phi_b$, the phase of the neuronal activity at the beginning of the stimulation. Such means can be a means for investigating the effect of the desynchronizing stimulus on the phase dynamics of the neuronal activity to be desynchronized. Such means can as has been indicated above by way of example, be a computer, an electronic circuit, a processor, a programmable electronic circuit (FPGA) or a computer program.

$\phi_e$ is thus the phase of the neuronal activity which is determined either directly after stimulation or with a constant time delay following stimulation. This time delay should preferably be smaller than one period length of the neuronal rhythm to be desynchronized or better still is equal to 0. Since the period length of the neuronal rhythm is varied with time, when the reference is made above to period lengths, the period length averaged over time is meant.

$\phi_b$ is the phase of the neuronal activity which is determined either directly at the point in time that the stimulation commences or at a constant time interval prior to the commencement of stimulation. The time interval should be, by analogy with the determination of $\phi_e$, as small as possible or better still equal to 0. The time interval in the determination of $\phi_e$ or $\phi_b$ should be as small as possible to ensure that time dependent variation in the period length will not influence the quality of the evaluation.

If the selected intensity of the sensory stimulus for desynchronization is too small, the phase resetting curve will typically have a mean rise of one. If, by contrast, the intensity is too large, the phase resetting curve will typically have a mean rise of 0.

The optimum intensity value and the optimum value for the lag between the last entrainment pulse and the desynchronizing pulse is determined with precision by the location in the phase resetting curve at which the transition from a mean rise 1 to a mean rise 0 occurs.

This has been shown in FIG. 5. FIG. 5*a* through 5*f* respectfully show phase resetting curves, whereby in the individual partial figures, the intensity of the sensory stimulus is constant but different from one of the partial figures to another and indeed increases from the smallest value in FIG. 5*a* to the largest value in FIG. 5*f*. The optimal stimulation parameter is thus found at the transition from FIG. 5*c* through 5*e* at the location marked by the arrow, (i) the mean value of the intensity belonging to FIGS. 5*c* and 5*d* is optimum for the selected stimulus duration at which the desynchronization intensity is the strongest and (ii) the inflection point indicated in FIG. 5*d* with the arrow indicates the phase $\phi_b$ which is optimal for the selected stimulus duration to which corresponds to the strongest desynchronizing time interval between the last stimulus of the entrainment and the desynchronizing stimulus. This time interval can either be given in absolute time values or, analogously thereto as illustrated in FIG. 5 in terms of the phase of the neuronal activity. With the phase resetting curves it is possible to provide a x-axis equivalent to $\phi_b$ giving an absolute time interval between the last excitation of the entrainment and the desynchronizing excitation. If the experimental data are strongly affected by noise, the phase resetting curve can be used to provide a pair of values comprised of intensity and $\phi_b$ by multiple measurements and the mean value of $\phi_e$ is then used.

The control unit 4 controls the sensory stimulation in two different ways. The need-controlled desynchronization can either be carried out repetitively or continuously. In both functional methods, an entrainment is used for the effective desynchronization. The frequency of the entrainment, that is the rate of the entraining sequence of sensory stimuli, is determined in a previous frequency scan. In that frequency scan it is determined which excitation frequency $f_A$ provides a maximum amplitude of the pathological rhythm. If the excitation frequency $f_A$ is identified or a plurality of excitation frequencies are identified, a desynchronization can be commenced. In the case that a plurality of excitation frequencies are found which lead to maxima in the amplitude of the pathological rhythm, the desynchronization is carried out for the one which has the strongest entrainment effect, that is the strongest excitation of the amplitude.

a) Repetitive Application:

In the repetitive application, the same desynchronizing stimulus or excitation sequence is repetitively applied. In the pauses between these desynchronizing stimulus or excitation sequences no stimulus or excitation is applied.

The patient is instructed before commencement of the need-control desynchronization by an investigator or by the device itself. That means that the patient is either told by the investigator how he or she should respond to the repetitively applied stimulation or excitation sequences or the device itself can signal this to the patient by for example by visual or auditory instruction: the patient hears or reads what he or she is to do.

Figure 6:
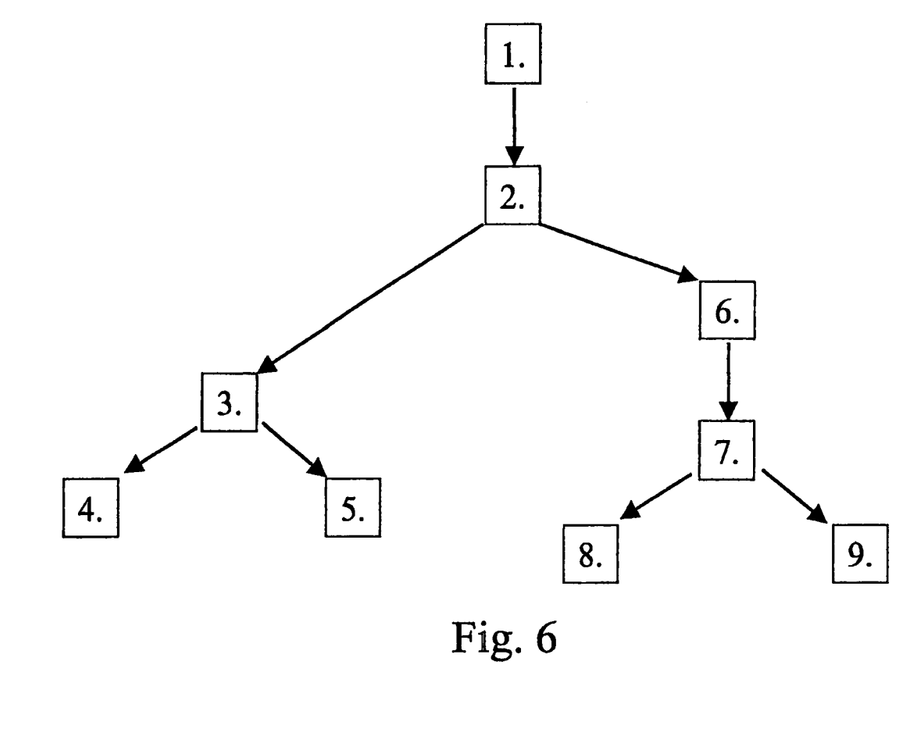

For example, the patient must try, upon visual stimulation with the repetitively applied visual stimulus pattern, of certain objects or individual patterns, for example Kanisza figures to compare them with one another or count them. The investigator controls, using the means 6 for monitoring the stimulation, preferably the effect of the stimulation of the brain activity and the information processing by the patient which is determined by feedback via the push button 5. The patient must for example, each time he recognizes a certain partial pattern, press the push button 5. In this manner the investigator is able to determine whether the applied sensory stimulus improves or enables the damping or suppression of the pathological rhythm. If the reaction of the patient is missed at least one time, an appropriate signal is provided by the control unit 4 to the means 6 for monitoring the stimulation and thus is communicated to the investigator. This signal serves to inform the investigator that the patient is not willing or is not capable of processing the sensory stimulus in accordance with the predetermined conditions.

The control unit 4 controls the application of the sensory stimuli in the following manner:

An entraining periodic sequence of sensory stimuli or excitation is applied with the optimum excitation frequency $f_A$. The sensory stimuli or excitation here used can be identical although they need not necessarily be identical. Preferably the sensory stimuli used with respect to the following parameters are identical in order to ensure an effective entrainment:

(i) They are of the same quality, that is that they deal for example always with the same visual pattern.

(ii) They have the same intensity, that is for example the same light or sound amplitude.

(iii) They have the same contrast, that is for example in the case of visual stimuli, the same light-dark contrast.

(iv) They have the same duration.

With a constant lag, there is thereafter effected an application of the desynchronizing stimulus or excitation in a vulnerable phase state of the pathological rhythm. The desynchronizing sensory stimulus is preferably of the same modality, that is, when the entraining stimuli are visual stimuli, the desynchronizing stimulus is also a visual stimulus and for example is without an auditory stimulus.

The desynchronizing stimulus need not however be of the same quality as the entraining stimuli. Preferably however it is of the same quality, that is it uses for example the same visual pattern. The desynchronizing stimulus differs however preferably from the stimuli of the entraining stimulus sequence by its duration and/or its intensity and/or its contrast.

As soon as the desynchronizing stimulus is applied, there is a transitory period in which no stimulus is present. In connection with this stimulus application, the patient advantageously must signal via the push button whether he has been able to detect for example special objects or visual patterns therein.

Following such a desynchronizing stimulus, there is a pause whose duration can lie within a statistical distribution in a predetermined interval, preferably a uniform distribution. During this pause no stimulus is applied. After this pause, there is a repetition of the collective of desynchronizing stimuli, comprised of another entraining stimulus sequence and an individual desynchronizing stimulus.

In the framework of the repetitive application, the control unit 4 determines whether the desynchronizing of the pathologically active neuronal population has been effected, that is whether the damping of the pathological rhythm has been strong enough. Should this be the case the repetition of the stimuli is continued. If the damping of the pathological rhythm is insufficient at least once, restandardization must be carried out with the above-described standardization procedure.

FIG. 2 shows an excitation with the resonance frequency which is followed by a desynchronization pulse in the vulnerable phase. In this Figure the x-axis represents the time and the y-axis the intensity of the sensory stimulus.

b) Continuous Application:

By contrast with the repetitive application (a) in the continuous application, there is a permanent sensory stimulus. Whenever the neuronal activity exceeds a threshold of the above-determined amplitude of the neuronal activity to be desynchronized, a desynchronization is carried out. For this purpose an entraining pulse sequence is followed by the application of at least one single stimulus (FIG. 2). In the time between the desynchronizations, a continuous sensory stimulation applies. In this case there are two possibilities:

I) In the time between the desynchronization, stimulation is carried out with a periodic sequence of sensory stimuli or excitation pulses. This sequence is comprised of identical individual stimuli which are applied at a frequency sufficiently different from the resonance frequency that no resonance arises.

II) In the time between the desynchronization, stimulation is applied with a random sequence of sensory stimuli or excitation pulses. The individual stimuli of this sequence are comprised of identical visual or auditory patterns in which the following parameters are statistically varied from stimulus or pulse to stimulus or pulse: with visual stimuli the contrast and/or the brightness can be varied. With auditory stimuli the sound volume can be varied. In addition, the pauses between the individual stimuli and the duration of the individual stimuli can be statistically varied. In the statistic variation, the corresponding parameters can be varied between the normal physiologically experimental limit or uniformly.

The purpose of the stimulation described above under I and II is, 1. to continuously supply sensory stimuli to patients which can be processed by them so that the patients can continuously have available the required action, for example, the detection of visual partial images, and 2. to prevent thereby a resonance of the pathological rhythm from developing.

FIG. 3a shows a sequence of stimuli by way of example for the means 1 for generating the sensory stimuli in the form of a time-spaced application of patterns as the sensory stimuli whereby variant I, that is a periodic stimulation between the desynchronization, is used. In FIG. 3b the associated activity pattern of the pathologically effected brain region has been given. In FIGS. 3a and 3b the x-axis is the time axis in each. In FIG. 3a the intensity of the stimulus is plotted along the y-axis. In FIG. 3b the amplitude is a function of time in a sliding time window for the neuronal activity to be desynchronized has been plotted.

In FIGS. 3a and 3b, the time regions $T_1$ and $T'_1$, $T_2$ and $T'_2$, $T_3$ and $T'_3$, $T_4$ and $T'_4$, as well as $T_5$ and $T'_5$ are identical. In the time regions $T_1$ or $T'_1$, the amplitude of the pathological rhythms because of resonance is a maximum. In the time regions $T_2$ or $T'_2$, a desynchronizing sensory stimulus is applied in the vulnerable phase to either completely suppress the pathological activity or at least reduce its intensity. This gives rise to a drop in the amplitude in FIG. 3b.

As has been described under I above in the time region $T_3$ a periodic stimulus sequence is applied whose frequency differs sufficiently from the resonance frequency in the time region $T_1$. The effect in the time region $T'_3$ is that in spite of the sensory stimulation the pathological rhythms will recover only slowly.

In the second case II, in the time region $T_3$, instead of a periodic stimulus sequence a random or stochastic stimulus sequence is used. With this feature the pathological rhythm is suppressed as long as possible.

In FIG. 3b this phase is characterized by the segment $T'_3$ in which the curve of the brain activity to be suppressed reaches its minimum value. As soon as the brain activity in the time region $T'_3$ again exceeds a threshold value, the need state for desynchronization arises so that in the next time region $T_4$ a new desynchronization operation is carried out. For this purpose in the time region $T_4$ the same entrainment is effected as in the time region $T_1$. Following the entrainment, in the time region $T_5$, a desynchronizing stimulus is applied as in the time region $T_2$. For this purpose the sensor 2 registers the increased activity of the pathologically affected brain region and reproduces the signal at the control unit 4 which triggers the next desynchronization. In conjunction with the desynchronization effected in the time region $T_5$, a periodic stimulus sequence is applied anew as in the time region $T_3$, with a frequency sufficiently different from the resonance frequency. It corresponds to the above-described case I. Alternatively thereto, also according to the above-described case II, stochastic or random stimulus sequences can be used.

The invention comprises a computer program with program code means for controlling a device which can carry out at least one of the preceding method steps or optional combinations of at least two of the method steps given in this description when the program is run on a computer. The invention also encompasses a computer program product with program code means which is stored on a computer-readable data carrier and permits the method to be carried out as defined by that computer program. This computer-program product can for example be a diskette. The invention also comprises an electronic circuit which is suitable for carrying out the instructions of the computer program or the computer program product.

The invention claimed is:

1. A device for desynchronizing pathologically rhythmic brain activity, the device comprising:
    a stimulator configured to generate a plurality of pulses at a plurality of excitation frequencies, respectively, to stimulate neuronal rhythmic activity in a patient's brain;
    a sensor configured to measure the neuronal rhythmic activity in response to the plurality of pulses; and
    a control unit configured to determine at least one frequency of the plurality of excitation frequencies in which the sensor measures a maximum excitation of the neuronal rhythmic activity in response to the plurality of pulses;
    wherein the control unit is further configured to control the stimulator to generate an entraining periodic pulse sequence operating at the at least one frequency to entrain the phase dynamic of the neuronal rhythmic activity,
    wherein the stimulator is further configured to generate a desynchronization pulse following the entraining periodic pulse sequence to desynchronize the neuronal rhythmic activity, and
    wherein the plurality of pulses, the entraining pulse sequence and the desynchronization pulse are either visual or acoustic or tactile.

2. The device according to claim 1, wherein the control unit is further configured to determine the vulnerable phase of the neuronal rhythmic activity, and wherein the stimulator is further configured to generate the desynchronization pulse at the vulnerable phase.

3. The device according to claim 2, wherein the control unit is further configured to determine optimal stimulation parameters based a series of test stimulations.

4. The device according to claim 3, wherein the control unit is further configured to determine a minimization of the amplitude of the neuronal rhythmic activity to be desynchronized.

5. The device according to claim 4, wherein the control unit is further configured to perform a Hilbert transformation to determine the minimization of the amplitude of the stimulation parameters.

6. The device according to claim 4, wherein the control unit is further configured to match a slowly changing sine function to a signal of the sensor in a time window following stimulation to determine the minimization of the amplitude of the stimulation parameters giving rise to a desynchronization of the neuronal rhythmic activity.

7. The device according to claim 4, wherein the control unit is further configured to integrate the amplitude of the power spectrum over the frequency band of signals measured by the sensor in a time window following the stimulation to determine the minimization of the amplitude of the stimulation parameters giving rise to a desynchronization of the neuronal rhythmic activity.

8. The device according to claim 2, wherein the control unit determines the vulnerable phase by varying the time spacing between the last excitation of the entraining periodic pulse sequence and the desynchronization pulse.

9. The device according to claim 8, wherein the control unit is further configured to effect a variation in the time spacing for different values of the intensity.

10. The device according to claim 8, wherein the control unit is further configured to increase the intensity in equidistant steps.

11. The device according to claim 1, wherein the control unit is further configured to calculate phase resetting curves.

12. The device according to claim 11, wherein the control unit is further configured to evaluate the phase resetting curves to measure the desynchronized neuronal rhythmic activity.

13. The device according to claim 12, wherein the control unit is further configured to apply the phase dynamic of the neuronal rhythmic activity before stimulation over the phase dynamic of the neuronal rhythmic activity after stimulation to evaluate the phase resetting curves.

14. The device according to claim 12, wherein the control unit is further configured to determine the position of the phase resetting curve at which the transition from a main rise 1 to a main rise 0 to evaluate the phase resetting curves.

15. The device according to claim 11, further comprising a display screen configured to display the phase resetting curves.

16. The device according to claim 11, wherein the control unit is further configured to quantitatively characterize calculate the phase resetting curves.

17. The device according to claim 1, wherein the control unit is further configured to determine the quality of the entrainment of the phase dynamic of the neuronal rhythmic activity.

18. The device according to claim 17, wherein the control unit is further configured to measure at least one of the phase dynamic and the amplitude of the neuronal rhythmic activity.

19. The device according to claim 18, wherein the control unit is further configured to perform means for determining the phase and amplitude of the neuronal rhythm to be desynchronized carries out a Hilbert transformation or a matching of the signals of the neuronal rhythmic activity with a slowly changing sine function in a sliding time window.

20. The device according to claim 1, wherein the sensor is further configured to measure the neuronal rhythmic activity before the stimulator generates a plurality of pulses, and wherein the control unit is configured to determine whether to perform need-controlled synchronization of the neuronal rhythmic activity of the patient's brain based on the neuronal rhythmic activity measured without stimulation.

21. The device according to claim 20, wherein the stimulator is further configured to generate a periodic succession of pulses to excite the neuronal rhythmic activity of the patient's brain.

22. The device according to claim 1, wherein the stimulator is at least one component selected from the group comprising a display screen, a pair of shutter-equipped eyeglasses, a loud speaker, headphones, a pressure generator and a time modulated laser.

23. The device according to claim 1, wherein the sensor is at least one component selected from the group comprised of a scalp EEG electrode and a MEG electrode.

24. The device according to claim 1, wherein the sensor is coupled to the control unit via an isolating amplifier.

25. The device according to claim 1, further comprising an input configured to receive feedback from the patient.

26. The device according to claim 1, wherein the sensor is further configured to evoke physiological and/or pathological brain activity.

27. The device according to claim 1, wherein the control unit is further configured to quantify the amplitude of the power spectrum over the plurality of excitation frequencies and to quantify the instantaneous amplitude of the plurality of excitation frequencies as determined by the Hilbert transformation.

28. The device according to claim 1, wherein the control unit is further configured to actuate the stimulator.

29. The device according to claim 1, wherein the control unit is further configured to execute a Fourier transformation or a wavelet analysis on the measured neuronal rhythmic activity.

30. The device according to claim 1 wherein the desynchronization pulse follows the entraining periodic pulse sequence with a predetermined time delay.

31. The device according to claim 1, wherein the stimulator is configured to vary the intensity of the plurality of pulses such that the control unit can determine an intensity at which the strongest desynchronization of pathologically rhythmic brain waves is effected.

32. The device according to claim 1, wherein the plurality of pulses range between frequencies of 1 and 100 Hz.

* * * * *

UNITED STATES PATENT AND TRADEMARK OFFICE
CERTIFICATE OF CORRECTION

PATENT NO.       : 8,543,219 B2
APPLICATION NO.  : 10/522933
DATED            : September 24, 2013
INVENTOR(S)      : Peter Tass Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1656 days.

Signed and Sealed this
Fifteenth Day of September, 2015

Michelle K. Lee
*Director of the United States Patent and Trademark Office*